United States Patent [19]

Hardtmann et al.

[11] 4,127,574

[45] Nov. 28, 1978

[54] 4-HYDROXY-3-SULFONYL-QUINOLIN-2(1H)-ONES

[75] Inventors: Goetz E. Hardtmann, Morristown; Gary M. Coppola, Parsippany, both of N.J.

[73] Assignee: Sandoz, Inc., E. Hanover, N.J.

[21] Appl. No.: 662,706

[22] Filed: Mar. 1, 1976

[51] Int. Cl.$^2$ .......................................... C07D 213/71
[52] U.S. Cl. .................................... 546/90; 424/258; 546/155
[58] Field of Search ...................... 260/289 K, 283 S; 424/258

[56] References Cited

U.S. PATENT DOCUMENTS 3,849,420  11/1974  Tong .................................. 260/283 S Primary Examiner—Donald G. Daus
Assistant Examiner—D. B. Springer
Attorney, Agent, or Firm—Gerald D. Sharkin; Richard E. Vila

[57] ABSTRACT

Anti-allergic 4-hydroxy-3-sulfonyl-quinolin-2(1H)-ones are prepared by reacting an isatoic anhydride with the carbanion resulting from the treatment of sulfonyl acetic acid alkyl esters with a proton abstracting agent.

22 Claims, No Drawings

4-HYDROXY-3-SULFONYL-QUINOLIN-2(1H)-ONES

This invention relates to chemical compounds which are 3-sulfonyl-4-hydroxy-quinolin-2(1H)-ones, to their preparation and to their use as pharmacological agents, particularly as anti-allergic agents.

In accordance with one aspect of the invention, the compounds of the formula I:

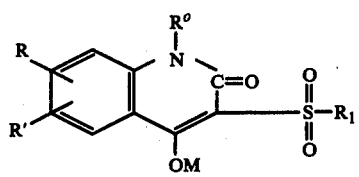

wherein

R° is hydrogen, alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl is of 3 to 6 carbon atoms and the alkyl portion is of 1 or 2 carbon atoms, or

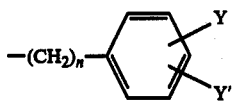

M is hydrogen or a cation derived from a proton abstracting agent, n is 0 or 1,

Y and Y' are independently hydrogen, halo of atomic weight of from 18 to 80, i.e., fluoro, chloro or bromo, alkyl of 1 to 3 carbon atoms, alkoxy of 1 to 3 carbon atoms or trifluoromethyl, R and R' are independently hydrogen, halo of atomic weight of from 18 to 80, i.e., fluoro, chloro, or bromo, alkyl of 1 to 4 carbon atoms, alkoxy of 1 to 4 carbon atoms, nitro or trifluoromethyl, with the proviso that only one of R and R' can be from the group consisting of nitro and trifluoromethyl, or R and R' together form 6,7-methylenedioxy, $R_1$ is alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl portion is of 3 to 6 carbon atoms and the alkyl portion is of 1 or 2 carbon atoms, or

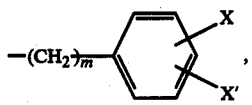

m is 0 or 1, and

X and X' are independently hydrogen, halo of atomic weight of from 18 to 80, i.e., fluoro, chloro or bromo, alkyl of 1 to 3 carbon atoms, alkoxy of 1 to 3 carbon atoms or trifluoromethyl, with the further proviso that the unsaturation in any alkenyl or alkynyl is on other than the alpha carbon atom, are prepared by reacting an isatoic anhydride of the formula II:

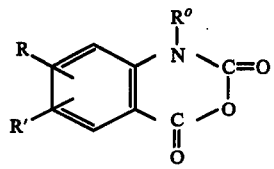

wherein R°, R' and R are as defined, with a compound of the formula III:

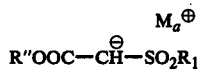

wherein $R_1$ is as defined above, R" is alkyl of 1 to 5 carbon atoms and $M_a$ is a cation derived from a proton abstracting agent, in the presence of an inert organic solvent, the resulting reaction product being treated with a proton source when a compound in which M is hydrogen is desired.

The preparation of Compounds I by reacting a Compound II with a Compound III may be carried out at temperatures generally in the range of from 20° C. to 200° C. in an inert organic solvent of conventional type, desirably an aprotic solvent, and under essentially anhydrous conditions. Examples of preferred solvents include dimethylacetamide, dimethylformamide and tetrahydrofuran, more preferably dimethylacetamide. Preferred temperatures are generally in the range of from 50° C. to 150° C. and it is usually preferred to initiate the reaction at a temperature in the range of from about 50° C. to 100° C. and then complete the reaction at a higher temperature above 100° C. up to 150° C. The mol ratio of Compound III to Compound II is not critical and is suitably in the range of 0.8:1 to 2:1, preferably about 1:1. Reaction times may vary fairly widely and can be typically of the order of 2 to 30 hours, more usually 5 to 20 hours. The reaction product of the Compounds II and III is a compound I in which M is the cation $M_a$. Such reaction product is treated in a conventional manner with a proton source to readily obtain the compounds I in which M is hydrogen when it is desired to obtain the Compounds I in which M is hydrogen. A wide variety of proton sources are known and may be employed, but it is generally preferred to employ aqueous mineral acid such as hydrochloric acid. The product of the formula I may be isolated and recovered from the resulting reaction mixture by working up by conventional techniques including, without limitation, crystallization, distillation and column chromatography. the reaction mixtures tend to be more complex when R° is hydrogen and such products of the formula I may be readily recovered by column chromatography.

The compound of the formula III is prepared in situ by reacting a compound of the formula IIIA:

wherein $R_1$ and R" are as above defined, a proton abstracting agent in an organic solvent which is of the type suitable for the reaction of Compounds II and III. Reaction temperatures may be generally of the order of from minus 100° C. to plus 150° C., but are preferably in the range of from 10° C. to 50° C. The proton abstracting agents are those which will dislodge a hydrogen atom from the methylene moiety of Compounds IIIA to result in the ionic product III with which the Compound II reacts to yield the desired Compound I. Such agents are of well known types and are represented by the stronger bases such as the alkali metal hydrides, the butyl lithiums and tertiary amines with the alkali metal hydrides being particularly preferred, e.g., sodium hydride and potassium hydride. In general, M is preferably an alkali metal, particularly sodium or potassium. The phrase "derived from a proton abstracting agent" as used in connection with the definition of M and $M_a$ is meant to designate the cation present in the proton abstracting agent and freed as a result of the reaction with the compound IIIA, e.g., sodium when sodium hydride is used, or the cation formed and resulting from such reaction, e.g., the ammonium ion when a tertiary amine is employed, as the case may be. The mol ratio of abstracting agent to the Compounds III may vary fairly widely but is most suitably at least about 0.8 to 1 and preferably between 0.9:1 to 1.5:1, more preferably 1:1 in the preferred modes of conducting the reaction. The resulting compound of the formula III in the organic solvent in which it is formed is used in preparing Compounds I by mixing such solution with Compound II or a solution of Compound II.

As will be evident, the Compounds I may be prepared in accordance with the reactions above-described by combining Compounds II, IIIA and a proton abstracting agent in an organic solvent and either: (i) regulating the temperature to form the Compound III without substantial reaction with Compound II followed by increasing the temperature to form the Compound I; or (ii) establishing a temperature within the range of from 20° C. to 150° C., whereby the Compounds I are prepared simultaneously with and in the presence of the formation of Compounds III. It is, however, preferred that the Compounds III being prepared prior to subjecting to conditions whereby such Compounds III react with Compounds II, and preparation of such Compounds III in the absence of Compounds II is usually the more preferred manner of preparation.

The compounds of the present invention contemplated as having anti-allergic activity are those of the formula IP:

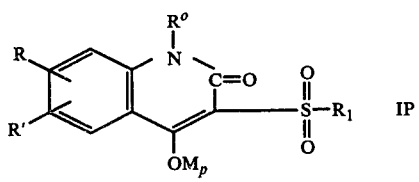

wherein $R^o$, R, R' and $R_1$ are as defined and $M_p$ is hydrogen or a cation forming a pharmaceutically acceptable salt. When preparing Compounds I in which M is a cation by the method of this invention, it is, of course, convenient and preferred to employ a proton abstracting agent which will result directly in a Compound I in which $M_a$ is a pharmaceutically acceptable cation, e.g., lithium, sodium, ammonium or potassium. In cases in which it may be desired to employ a proton abstracting agent which will not result in a pharmaceutically acceptable cation or in which it is desired to replace one pharmaceutically acceptable cation for another, such cations may be exchanged for the desired pharmaceutically acceptable cation by conventional and well known salt exchange procedures.

The compounds of the formula II and IIIA are each either known per se or may be prepared from known materials by procedures established for the known compounds.

The compounds of formula IP are useful because they possess pharmacological activity in animals. In particular they possess disodium chromoglycate (DSCG)-like activity, in particular histamine release inhibiting activity, and are therefore useful in the treatment of allergic conditions, such as allergic asthma, as indicated in the passive cutaneous anaphylaxis test in the rat. Female rats (180–200 g) are sensitised by intramuscular administration of 2 mg of egg albumin (Merck Nr. 967) dissolved in 0.1 ml of physiological saline and 0.5 ml of Haemophiluspertussis vaccine (Schweizerisches Serum and Impfinstitut, Bern; Nr. 115 325; $4 \times 10^{10}$ organism/ml) intraperitoneally. Fourteen days later, the animals are exsanguinated, the blood centrifuged, the serum collected and deep frozen. The serum thus obtained (anti-serum) is injected intradermally (0.1 ml of a 1:2 diluted serum per injection site) at four sites on the backs of untreated, female rats. Twenty-four hours later each rate is administered 3.2 mg/kg i.v. or 32 mg/kg p.o. of the test compound, and either immediately or 5 or 30 minutes afterwards, in the case of intravenous administration, or 60 minutes afterwards, in the case of oral administration, afterwards egg albumin (5 mg/ml i.v.) dissolved in physiological saline containing 0.25% Evans Blue dye (Merck Nr. 3169). The egg albumin elicits a cutaneous anaphylactic reaction, the intensity of which is proportional to the extent to which the Evans Blue dye diffuses into the tissue surrounding each of the four sensitisation sites. Thirty minutes after the administration of the egg albumin, the rats are killed with ether, the underside of the skin of the back of each animal is exposed and the diameter of the areas of blue dye surrounding each of the four sensitisation sites are measured. Each dose of test compound is investigated in between four and six rats and the mean diameter compared with the mean value obtained in four solvent-treated control rats. The percentage inhibition is taken as the percentage of the mean diameter in the test animals relative to the mean diameter in the controls.

The DSCG-like activity, in particular histamine release inhibiting activity, can be confirmed by inhibition of histamine release in the rat peritoneal mast cell test, basically as described by Kusner et al., J. Pharmacol. Exp. Therap. 184, 41–46 (1973), with the following modification: after sedimentation of the mast cells by centrifugation at $350 \times g$ and 4° C., the sediments are taken up in 1 ml of Hank's balanced salt solution (HBSS) (buffered to a pH of 6.9) and pooled. The resulting suspension is centrifuged, washed again with HBSS and sedimented. The thus purified mast cells are prepared as 2 ml suspensions in HBSS. To these are added either 2 ml of HBSS, to determine the spontaneous histamine release, or 2 ml of HBSS and 2.24 ug of compound 48/80 (N-methylhomoanisylamineformaldehyde condensate; a histamine liberator from Burroughs Wellcome and Co. Inc., Tuckahoe, N.Y. USA), to determine the 48/80 induced histamine release, or 2 ml of HBSS with 2.24 ug of 48/80 and from 18 to 180 ug/ml of the test compound, to determine the 48/80 induced histamine release in the presence of the test compound.

The 48/80 induced histamine release minus the spontaneous histamine release is taken as 100% histamine release. The 48/80 induced histamine release in the presence of the test compound minus the spontaneous histamine release is then compared with the 100% value to determine the percentage inhibition by the test compound. [The histamine determination is effected in conventional manner, for example as described in the above-mentioned Kusner et al. article, or in Kusner and Herzig, Advances in Automated Analysis, 429 (1971)].

For the above-mentioned use, the dosage administered will, of course, vary depending on the compound employed, mode of administration and treatment desired. However, satisfactory results are generally obtained on administration at a daily dosage of from about 1 to 100 mg/kg of animal body weight, conveniently given in divided doses two to four times daily, or in sustained release form. For the larger mammals, the total daily dosage is in the range of from about 60 to 1000 mg of the compound admixed with a solid or liquid pharmaceutical carrier, for administration orally, and divided dosage forms comprise 15 to 500 milligrams of the compound in admixture with a solid or liquid pharmaceutical carrier.

A representative formulation for administration 2 to 4 times a day for treatment of allergic asthma is a capsule prepared by standard techniques to contain the following:

| Ingredient | Weight (mg) |
| --- | --- |
| 1-methyl-4-hydroxy-3-methylsulfonyl-quinolin-2(1H)-one | 70 |
| Kaolin | 210 |

The following examples are given for purposes of illustration only.

EXAMPLE 1

1-methyl-4-hydroxy-3-methylsulfonyl-quinolin-2(1H)-one

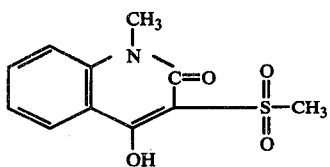

To a solution of 6.7 g. of ethyl methylfulfonylacetate in 30 ml. of anhydrous dimethylformamide is added portion-wise 1.7 g. of pentane washed 56% sodium hydride whereby hydrogen gas is released. The resulting solution is stirred at room temperature for 15 minutes. The temperature of the resulting mixture is then raised to 120° C. and there is added dropwise a solution of 7.2 g. of N-methyl isatoic anhydride in 30 ml. of dimethylacetamide causing the release of carbon dioxide. The resulting solution is then heated with stirring at 120° C. for 18 hours, the dimethylacetamide stripped off in vacuo, water added to the residue and the resulting aqueous system extracted with methylene chloride. The aqueous phase is acidified with 2N. hydrochloric acid to obtain a precipitate which is filtered off, washed with water, dried and recrystallized from methylene chloride/diethylether to obtain 1-methyl-4-hydroxy-3-methylsulfonyl-quinolin-2(1H)-one, m.p. 169°–172° C.

EXAMPLE 2

Following the procedure of Example 1, the following compounds are prepared:
(A) 1-methyl-4-hydroxy-3-phenylsulfonyl-quinolin-2(1H)-one, m.p. 212°–214° C.
(B) 1-propargyl-4-hydroxy-3-methylsulfonyl-quinolin-2(1H)-one, m.p. 206°–209° C.
(C) 1-allyl-4-hydroxy-3-phenylsulfonyl-quinolin-2(1H)-one, m.p. 186°–189° C.
(D) 1-methyl-6-chloro-4-hydroxy-3-phenylsulfonyl-quinolin-2(1H)-one, m.p. 254°–256° C.
(E) 1-benzyl-4-hydroxy-3-methylsulfonyl-quinolin-2(1H)-one.
(F) 1-methyl-4-hydroxy-3-(p-methoxyphenylsulfonyl)-quinolin-2(1H)-one, m.p. 203°–206° C.
(G) 1-(p-chlorobenzyl)-4-hydroxy-3-methylsulfonyl-quinolin-2(1H)-one.
(H) 1-methyl-6,7-dimethoxy-4-hydroxy-3-phenylsulfonyl-quinolin-2(1H)-one, m.p. 285°–287° C.
(I) 1-phenyl-4-hydroxy-3-ethylsulfonyl-quinolin-2(1H)-one.
(J) 1-cyclopropylmethyl-4-hydroxy-3-methylsulfonyl-quinolin-2(1H)-one.
(K) 4-hydroxy-3-methylsulfonyl-quinolin-2(1H)-one.
(L) 4-hydroxy-3-phenylsulfonyl-quinolin-2(1H)-one.
(M) 1-allyl-4-hydroxy-3-methylsulfonyl-quinolin-2(1H)-one, m.p. 117°–120° C.
(N) 1,6,8-trimethyl-4-hydroxy-3-methylsulfonyl-quinolin-2(1H)-one.
(O) 8-methyl-4-hydroxy-3-methylsulfonyl-quinolin-2(1H)-one.
(P) 1-methyl-4-hydroxy-3-allylsulfonyl-quinolin-2(1H)-one.
(Q) 1-allyl-4-hydroxy-3-allylsulfonyl-quinolin-2(1H)-one.
(R) 1-propargyl-4-hydroxy-3-phenylsulfonyl-quinolin-2(1H)-one, m.p. 233°–235° C.
(S) 1-methyl-4-hydroxy-3-(p-chlorophenylsulfonyl)-quinolin-2(1H)-one, m.p. 233°–234° C.
(T) 1-methyl-6,7-methylenedioxy-4-hydroxy-3-methylsulfonyl-quinolin-2(1H)-one, m.p. 263°–265° C.

Pharmaceutical compositions provided by the invention and useful for treating allergic conditions due to histamine release contain a compound of the formula IP as active ingredient and one or more conventional pharmaceutically acceptable carriers, and such other conventional adjuvants as may be desired or necessary. Such compositions may be in conventional orally administerable forms such as tablets, capsules, granules, dispersible powders, elixirs, syrups, suspensions and the like or in conventional parenterally administerable forms such as an injectable sterile solution, suspension or the like, e.g., a sterile injectable aqueous suspension. Such compositions including applicable unit dosage forms thereof may be prepared according to any method known in the art for the manufacture of pharmaceutical compositions. In general, the compositions of the invention adapted for either oral or parenteral administration may contain from 1 to 90% by total weight of active ingredient in combination with the carrier, more usually 3 to 70%. The preferred unit dosage forms are the essentially solid forms adapted for oral administration, e.g., tablets or capsules.

What is claimed is:
1. A compound of the formula:

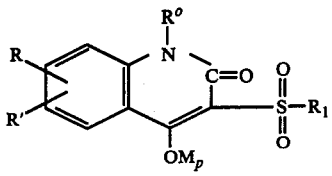

wherein

R° is hydrogen, alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl is of 3 to 6 carbon atoms and the alkyl portion is of 1 or 2 carbon atoms, or

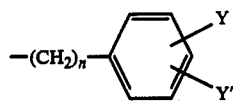

$M_p$ is hydrogen or a cation forming a pharmaceutically acceptable salt, $n$ is 0 or 1, Y and Y' are independently hydrogen, fluoro, chloro, or bromo, alkyl of 1 to 3 carbon atoms, alkoxy of 1 to 3 carbon atoms or trifluoromethyl, R and R' are independently hydrogen, fluoro, chloro, bromo, alkyl of 1 to 4 carbon atoms, alkoxy of 1 to 4 carbon atoms, nitro or trifluoromethyl, with the proviso that only one of R and R' can be from the group consisting of nitro and trifluoromethyl, or R and R' together form 6,7-methylenedioxy, $R_1$ is alkyl of 1 to 6 carbon atoms, alkenyl of 3 to 6 carbon atoms, alkynyl of 3 to 6 carbon atoms, cycloalkyl of 3 to 6 carbon atoms, cycloalkylalkyl in which the cycloalkyl portion is of 3 to 6 carbon atoms and the alkyl portion is of 1 or 2 carbon atoms, or

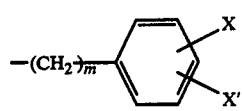

$m$ is 0 or 1, and

X and X' are independently hydrogen, fluoro, chloro, bromo, alkyl of 1 to 3 carbon atoms, alkoxy of 1 to 3 carbon atoms or trifluoromethyl with the further proviso that the unsaturation in any alkenyl or alkynyl is on other than the alpha carbon atom.

2. A compound of claim 1 in which $R_1$ is alkyl.
3. A compound of claim 2 in which R° is alkyl.
4. A compound of claim 2 in which R° is alkenyl.
5. A compound of claim 2 in which R° is alkynyl.
6. A compound of claim 2 in which R° is cycloalkyl or cycloalkylalkyl.
7. A compound of claim 2 in which R° is $$-(CH_2)_n-\phantom{X}\begin{array}{c}Y\\Y'\end{array}$$

8. A compound of claim 7 in which $n$ is 1.
9. A compound of claim 2 in which R° is hydrogen.
10. A compound of claim 1 in which $R_1$ is alkenyl.
11. A compound of claim 10 in which R° is alkyl.
12. A compound of claim 10 in which R° is alkenyl.
13. A compound of claim 1 in which $R_1$ is cycloalkyl or cycloalkylalkyl.
14. The compound of claim 1 which is 1-methyl-4-hydroxy-3-methylsulfonyl-quinolin-2(1H)-one.
15. The compound of claim 1 which is 1-benzyl-4-hydroxy-3-methylsulfonyl-quinolin-2(1H)-one.
16. The compound of claim 1 which is 1-(p-chlorobenzyl)-4-hydroxy-3-methylsulfonyl-quinolin-2(1H)-one.
17. The compound of claim 1 which is 1-methyl-6,7-dimethoxy-4-hydroxy-3-phenylsulfonyl-quinolin-2(1H)-one.
18. The compound of claim 1 which is 1-allyl-4-hydroxy-3-methylsulfonyl-quinolin-2(1H)-one.
19. A compound of claim 1 in which $M_p$ is hydrogen.
20. A compound of claim 1 in which R and R' are independently hydrogen, fluoro, chloro, bromo, alkyl of 1 to 4 carbon atoms, alkoxy of 1 to 4 carbon atoms, nitro or trifluoromethyl.
21. A compound of claim 20 in which R and R' are independently hydrogen, fluoro, chloro, bromo, alkoxy of 1 to 4 carbon atoms or alkoxy of 1 to 4 carbon atoms.
22. A compound of claim 1 in which R and R' together form 6,7-methylenedioxy.

* * * * *